(12) United States Patent
Yin et al.

(10) Patent No.: US 11,399,766 B2
(45) Date of Patent: Aug. 2, 2022

(54) FETAL MONITORING SYSTEM AND METHOD

(71) Applicant: KONINKLIJKE PHILIPS N.V., Eindhoven (NL)

(72) Inventors: Bin Yin, Shanghai (CN); Sheng Jin, Shanhai (CN); Mingdong Li, Shanghai (CN); Yuqiang Wu, Shanghai (CN); Lin Li, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 349 days.

(21) Appl. No.: 16/062,257

(22) PCT Filed: Dec. 9, 2016

(86) PCT No.: PCT/EP2016/080355
§ 371 (c)(1),
(2) Date: Jun. 14, 2018

(87) PCT Pub. No.: WO2017/102566
PCT Pub. Date: Jun. 22, 2017

(65) Prior Publication Data
US 2018/0368753 A1    Dec. 27, 2018

(30) Foreign Application Priority Data

Dec. 18, 2015  (WO) ................ PCT/CN2015/097909
Mar. 31, 2016  (EP) ..................................... 16163215

(51) Int. Cl.
*A61B 5/00*        (2006.01)
*A61B 7/00*        (2006.01)
(Continued)

(52) U.S. Cl.
CPC ........ *A61B 5/4362* (2013.01); *A61B 5/02411* (2013.01); *A61B 5/344* (2021.01);
(Continued)

(58) Field of Classification Search
None
See application file for complete search history.

(56) References Cited

U.S. PATENT DOCUMENTS 4,781,200 A      11/1988  Baker
5,605,155 A  *    2/1997  Chalana ............... A61B 5/1075
                                                   600/443
(Continued)

FOREIGN PATENT DOCUMENTS

CN      103222862 A      7/2013
CN      103845060 A      6/2014
(Continued)

OTHER PUBLICATIONS

PCT International Search Report, International application No. PCT/EP2016/080355, dated Mar. 1, 2017.
(Continued)

*Primary Examiner* — Alex M Valvis
*Assistant Examiner* — Aurelie H Tu

(57) ABSTRACT

A system and method is provided for monitoring the fetal position and/or orientation of the fetus of an expectant mother. An acoustic sensor array is positioned over the belly. The pattern of acoustic sensor signals is processed to determine a fetal orientation and/or to determine movement over time of the fetus.

15 Claims, 9 Drawing Sheets

(51) Int. Cl.
  *A61B 5/344* (2021.01)
  *A61B 5/024* (2006.01)
  *A61B 5/11* (2006.01)
(52) U.S. Cl.
  CPC ............ *A61B 5/6823* (2013.01); *A61B 7/00* (2013.01); *A61B 5/1117* (2013.01); *A61B 5/4343* (2013.01); *A61B 5/6831* (2013.01); *A61B 2503/02* (2013.01); *A61B 2562/0204* (2013.01); *A61B 2562/04* (2013.01); *A61B 2562/046* (2013.01)

(56) References Cited

U.S. PATENT DOCUMENTS

| | | | |
|---|---|---|---|
| 5,795,296 A * | 8/1998 | Pathak | A61B 5/1075 600/443 |
| 8,730,166 B2 | 5/2014 | Larsen | |
| 2007/0213627 A1 | 9/2007 | James | |
| 2009/0093717 A1 * | 4/2009 | Carneiro | A61B 8/0866 600/443 |
| 2009/0299212 A1 * | 12/2009 | Principe | G06F 19/00 600/547 |
| 2010/0076330 A1 * | 3/2010 | Kimura | A61B 5/4362 600/511 |
| 2010/0185108 A1 * | 7/2010 | Vullings | A61B 5/0444 600/511 |
| 2011/0282199 A1 * | 11/2011 | Lee | A61B 5/1075 600/437 |
| 2014/0228653 A1 * | 8/2014 | Kiraly | A61B 5/4362 600/301 |
| 2016/0081663 A1 * | 3/2016 | Chen | A61B 8/0866 600/425 |
| 2016/0374608 A1 * | 12/2016 | Dugan | A61B 5/1114 600/301 |

FOREIGN PATENT DOCUMENTS

| | | |
|---|---|---|
| CN | 104306018 A | 1/2015 |
| CN | 104586405 A | 5/2015 |
| KR | 20080057858 A | 6/2008 |

OTHER PUBLICATIONS

Observations on the PCT International Search Report and the Written Opinion of International Application No. PCT/EP2016/080355, dated Apr. 7, 2017.

* cited by examiner

FETAL MONITORING SYSTEM AND METHOD

CROSS-REFERENCE TO RELATED APPLICATIONS

This application claims the priority benefit under 35 U.S.C. § 371 of International Patent Application No. PCT/EP2016/080355, filed Dec. 9, 2016, which claims the benefit of International Application No. PCT/CN2015/097909 filed on Dec. 18, 2015, and claims the benefit of European Patent Application No. EP16163215.3, filed Mar. 31, 2016. These applications are hereby incorporated by reference herein in their entirety.

FIELD OF THE INVENTION

This invention relates to a fetal monitoring system and method.

BACKGROUND OF THE INVENTION

Fetal movement is of great importance for evaluating fetal health and wellbeing. Fetal movement may refer to any kinds of movement of any part of the fetus. Intact neuromuscular functions and an adequate supply of oxygen and nutrients to the central nervous system are needed for normal fetal movement. Actual decreases in fetal movement may indicate fetal compromise or predict poor fetal outcome. Pregnant women are suggested by healthcare providers to count fetal movement at least once every day, starting from the 2nd trimester. An average of 3~5 times per hour indicates the fetus is doing well. Too few or too many movements can be caused by a shortage of oxygen supply, which requires healthcare providers to be contacted.

Besides the clinical indications, information about the fetal movement and position may provide expectant parents with the knowledge of how the fetus is doing, which gives pleasure and reassurance. This fetal diary or actigraph type of fetal activity recording, without explicit clinical implication, serves as an emotional link between the mother-to-be and the fetus.

Automation in recording the fetal position and orientation information would be of great benefit. It is unrealistic to perform manual counting of fetal movements and subjective judgment of fetal position, in particular over a prolonged time period. A wearable monitoring device would therefore be of interest that is easy to use, cost-effective, safe for continuous usage, and able to record and extract fetal movement and position information in an automatic fashion.

In this context, "fetal orientation" refers to the angle of the fetal long axis to that of the mother and "center of distribution" refers to the geometric center of the sound pressure distribution on maternal abdomen. The center of distribution indicates the "fetal position", which refers to the location of the fetus relative to the geometric center of pregnant woman's abdomen. Fetal position and/or orientation change over time during the pregnancy, as a result of the fetal movement. Towards the date of delivery, the fetus becomes restricted in the uterus due to its growing size, and its orientation has direct implication on whether there might be intrapartum complications.

If a system is for home and continuous monitoring, ultrasound and galvanic technologies are not suitable, such as those that are adopted by most of the existing fetal monitoring products, either for medical or for consumer applications. Furthermore, current fetal monitors utilize a single probe that is not able to catch the fetal position or orientation information due to the lack of spatial resolution.

CN104306018 discloses a method which uses a set of "sound collectors" (microphones) to locate the fetal heart position by identifying the point where the sound signal is maximal. The orientation of the fetus can be determined based on the location of fetal heart, while the fetal movement, defined as the displacements of the location of fetal heart over a certain threshold, can be monitored as well.

In this system, it is difficult to find one point where the signal is the strongest since there might be several points sharing similar signal strength whose effective acoustic paths are similar The effective acoustic path depends on the thickness, density and Young's module of the abdomen compositions. The position with the strongest signal may also not correspond to the projection of the fetal heart on the belly. U.S. Pat. No. 4,781,200A discloses a fetal monitoring system comprising a sensor garment to continuously detect physical movement of the fetus within the mother and provide at least one electronic fetal movement sensor signal which is indicative of fetal movement, and a computing means to receive and analyze said cardiac and movement sensor signals to determine fetal heart rate and including means to perform at least one analysis relating fetal heart rate and detected movement by the fetus. The accelerometer is implemented as the movement sensor for fetal movement detection.

US 20070213627A1 discloses an apparatus for monitoring fetal behavior, the apparatus comprising an input for receiving ECG data from a set of electrodes attached to a maternal body, a waveform pre-processor for identifying a succession of fetal ECG complex waveforms within the received data, a waveform processor for determining differences in the succession of fetal ECG complex waveforms over time and an event logger determining from the determined differences a number of fetal movements during the period of time.

SUMMARY OF THE INVENTION

There is a need for detecting the fetal position and movement accurately and with a low cost, comfortable and easy-to-use system.

The invention is defined by the claims.

According to examples in accordance with an aspect of the invention, there is provided a system for monitoring the fetal movement of the fetus of an expectant mother, comprising:

an acoustic sensor array for positioning over the belly, each acoustic sensor of the acoustic sensor array configured to receive an acoustic signal generated by fetal heartbeat; and a processor for processing the acoustic sensor signals received continuously over a predetermined time period, wherein the processor is adapted to determine a center of distribution from the acoustic sensor signals received each time and determine a fetal orientation and/or a fetal position from the distribution of acoustic signals to determine a fetal movement by detecting a change in the position of the center of distribution.

In this system, the fetal heart beat is used as a sound source. The sound wave generated propagates through the belly via acoustic paths and arrives on a portion of the belly of the expectant mother. Each acoustic path crosses through the fetal chest, amniotic fluid, uterine wall and mother's belly wall, each of which constitutes a respective portion of the whole path. Fetal orientation and fetal position will impact on the constitution of each acoustic path. Therefore, different locations of the acoustic sensors lead to multiple acoustic path(s) of different characteristics for the sound response, which will influence the sound signal finally received by the sensor attached to or placed on the portion of the expectant mother. Each sound signal received by an acoustic sensor is an integration of the sound waves propagating through different paths and arriving at the same acoustic sensor. Furthermore, when the fetal orientation or fetal position changes, the acoustic paths change accordingly, which will also have impacts on the received sound signals. The correlation between the fetal orientation, the fetal position, the strength of the sound signal received and the location of acoustic sensors, provides a basis for a determination of the fetal orientation or the fetal position. Such correlation may be predetermined by simulation or measurement. In this way, the invention provides a feasible and accurate solution to enable the fetal orientation or position monitoring. The acoustic signals are monitored continuously for a predetermined duration. A center is determined from the distribution of acoustic sensor signals received each time, the position change of which indicates by a change in the overall pattern of the received acoustic signals. As for implementation, the center of distribution may follow the definition of the center of mass, and each sound pressure is considered as a discrete mass located on the abdomen, where the force moment from each sensor to the center keeps the same. Center of distribution may also be defined as the center of the spatial distribution of the valid sound pressures, where the sound pressure is considered as valid under predefined criteria, for example, a value threshold. The sound signal may also be termed as "sound pressure" in view of the working principle of particular acoustic sensor, for example microphone, which picks up the sound signal through the its membrane for the sound pressure generated by the sound wave.

In the early stage of a pregnancy, both the center of distribution of the acoustic signal pattern and the orientation are of great importance for fetal movement determination. In the late stage of pregnancy, fetal orientation is more important than the center of distribution, since the fetus may be too big to have significant changes in the center of distribution.

The acoustic sensor array for example is integrated into a belly belt that can be worn comfortably over a prolonged time period. By analyzing the sound distribution patterns (rather than an individual sensor signal), detailed information of fetal orientation, movement and also position can be extracted.

The pattern of sensor signals may be used for orientation and position tracking. Position tracking of course amounts to tracking the movement. Thus, instead of finding a best sensor signal and then analyzing that signal, the information is extract from patterns of signals. These patterns may be identified by linearly combining individual sensor signals, or other pattern recognition approaches.

Pattern recognition approaches may be used to associate detected patterns with reference patterns.

Pattern analysis may also be used to determine a center of distribution location, and the movement of this location may be tracked. It may or may not correspond in a predictable way to the sound source (i.e. heart) location.

The fetal movement, including position and orientation, can be monitored automatically over a prolonged time period. Instead of trying to find one point indicating the heart position, a sound pressure pattern (distribution) is recorded using the sensor array. The processing of an array of sensor data enables more detail to be obtained concerning the fetal movement and/or the position and orientation, such as the fetal movement type. Different movement types are for example drifting, rolling, or rotating. This detailed information may be used to build an augmented reality model of the fetus that can be shown on display devices like mobile phones or even projected onto the belly.

There may be an array of at least 5 sensors. There may for example be 10 or more sensors, 20 or more sensors or possibly even more than 30.

The sensor array preferably comprises an array of passive sound sensors. This means the system is low cost and has low power consumption, by avoiding the need for signal sources, such as ultrasound emitters, and this also means the system is safe for the use by a consumer. The sound sensors may simply comprise microphones or other pressure sensor devices. Any type of microphone may be used, such as electromagnetic, capacitive, piezoelectric or optical.

The processor may be adapted to determine a fetal orientation from the acoustic sensor signals by analyzing the pattern of sensors signals from the acoustic sensor array.

Thus, based on pattern matching or best fit matching to a set of template (reference) patterns, a fetal orientation may be obtained. The fetal orientation may be as simple as head up or head down, or there may be more positions that may be detected.

The processor may be adapted to determine fetal movement from the acoustic sensor signals by detecting a change in the overall pattern of acoustic sensor signals over a predetermined time period, which change meets a threshold criterion. Fetal movement may instead or additionally be based on a change over time of the fetal orientation.

A change in the pattern received will be caused by a change in the position of the signal source, i.e. the fetal heart, and by the changed tissue pattern between the signal source and the sensor array.

The processor may be adapted to determine a duration of a movement event by counting the number of successive predetermined time periods during which there is determined movement.

The predetermined time period may be in the range 0.05 s to 1 s, so that the sampling frequency of the sensor signal pattern is of the order of a few to a few tens Hz.

The processor may be adapted to classify determined movements as a single movement event when a minimum number of successive predetermined time periods is reached during which there is detected movement. Sequential movements may be classified as the same movement event if they are separated by a maximum number of successive periods without detected movement.

For example, a movement event may be defined as lasting at least 2 seconds, which would mean at least 4 successive detected movements are needed for a sampling period of 0.5 s (2 Hz).

The processor may be adapted to classify a determined movement as a fetal position change when the change in center of distribution position exceeds a threshold. Unlike adults, the fetal heart is located close to the geometric center of the fetus, therefore the fetal position change usually causes a relative larger displacement of the center of the distribution position than that caused by fetal orientation change or the movement of the fetal body parts, for example the kicking of the fetal legs. Then the threshold is for example larger than the threshold just for detecting movement, which may then be caused by a pure fetal orientation change. Thus the system can differentiate between fetal movement and adjustment of the fetal position or orientation. The fetal position change will be monitored and differentiated from other fetal movements, such as fetal orientation change or body parts movement, which provide a more accurate description of the fetal behavior for further analysis, for example, an alarming of abnormal fetal development or a vivid display of the fetal status to the end user.

The processor is adapted to classify a determined movement as fetal orientation change or fetal position change by pattern recognition based on a training database of acoustic signal distributions. Duet to the geometry of the fetus as mentioned, the fetal orientation is difficult to be determined based on a single point with the strongest acoustic signal as indicated in the prior art cited in the background, where even such "single" point may not exist due to the possibility that multiple points with the same strength/pressure may exist due to multiple paths propagation effects. Furthermore, such fetal orientation change is difficult to distinguish from the movement of the body parts. Therefore pattern recognition based training sound pressure distributions can be implemented for the determination of the fetal orientation change, as the different properties of propagation paths formed by different fetal orientations will cause the change of the acoustic signal distributions received on the belly. Such change will easily be distinguished from the change caused by the movement caused by the body parts, since the influence of the movements of the body parts will only be partial and much smaller. The pattern recognition can also be applied to fetal position change.

The processor may further be adapted to classify a determined movement as a fetal position change when the new position remains constant for particular time period. The particular time period may be varied in dependence on the gestational stage, for example ranging from a few minutes (e.g. 5 minutes) to an hour. A position change is thus a movement that ends at a different position from that when it begins.

The data sampling period, which defines the two sequential time instants at which the positions are compared, may also be adjusted in dependence on the gestational stage. For example as the delivery date is approached the data sampling period may be increased, for example to a value between 10 minutes and 1 hour. The movement frequency drops for example due to the reduction in the intrauterine space.

The system may comprise a memory and a data transmission unit for transmitting the acoustic sensor data to the processor or to the memory, in a wired or wireless fashion. The data may thus be stored for logging purposes. The data processing may be carried out at the sensor array or remotely. The data processing may be in real time or it may be off-line.

A user interface device is preferably provided for presenting the results of the processing to the user. This is for example in the form of a display device.

Examples in accordance with another aspect of the invention provide a method for monitoring the fetal movement, comprising:

sensing acoustic signals at the belly of the expectant mother using an array of acoustic sensors, wherein the strength of the acoustic signal received by each acoustic sensor is dependent on the fetal orientation, the fetal position and the location of the acoustic senor; and processing the acoustic sensor signals received continuously over a predetermined time period, determining a center of distribution from the acoustic sensor signals received each time;

determining a fetal movement by detecting a change in the position of the center of distribution.

This method makes use of a sensor array to enable fetal movement to be monitored automatically over a prolonged time period.

A fetal orientation may be determined from the acoustic sensor signals by analyzing the pattern of sensors signals from the acoustic sensor array, for example by comparing the pattern of sensors signals from the acoustic sensor array with predetermined reference patterns.

Fetal movement may be determined by detecting a change in the overall pattern of acoustic sensor signals over a predetermined time period, which change meets a threshold criterion. This may be implemented by determining a center of distribution of the acoustic sensor signals, and characterizing the change by a change in the center of distribution position.

The duration of a movement event may be obtained by counting the number of successive predetermined time periods during which there is determined movement.

The method may comprise deriving a predictive model based on training data. The training process may for example involve detecting and recording the sound pressure pattern of the fetal heart sound and analyzing the pattern using actual fetal orientations, for example as detected by a sonograph. The pattern analysis may involve selecting data features from the pattern, such as the relationship between different sensor signals, or a particular combination of sensor signals.

The processing implemented within the system may be carried out by a computer program.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a system and method for monitoring the fetal position and/or orientation of the fetus of an expectant mother. By tracking position changes, movement can also be monitored. An acoustic sensor array is positioned over the belly. The pattern of acoustic sensor signals is processed to determine a fetal orientation and/or to determine a position and therefore movement over time of the fetus.

Figure 1:
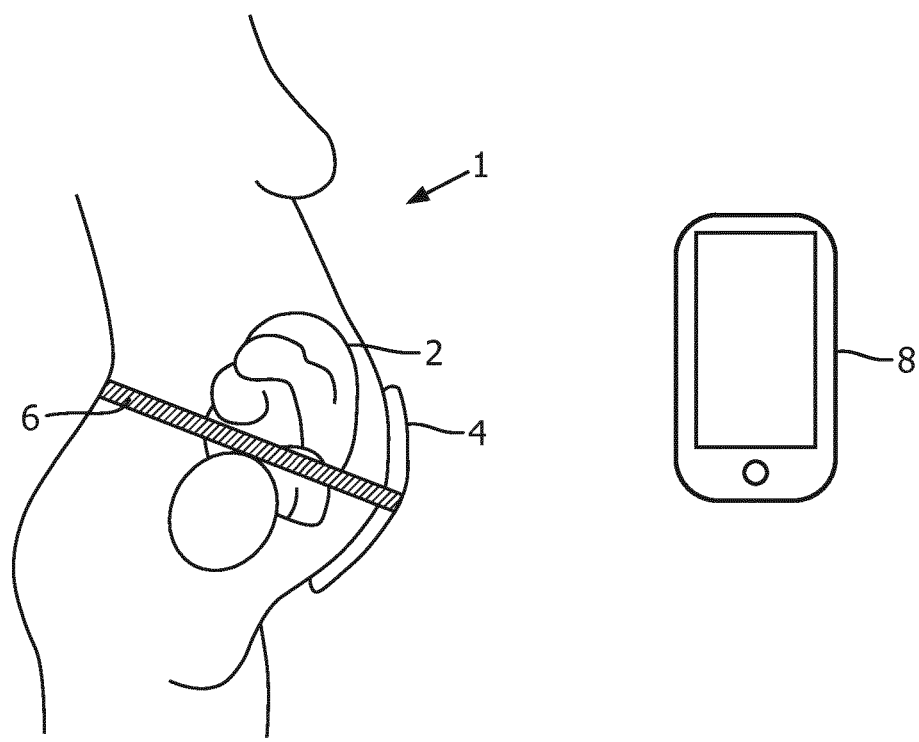
FIG. 1 shows a system for monitoring the motion of the abdomen of an expectant mother.

FIG. 1 shows one example of the system being worn by an expectant mother 1. The system is for monitoring the fetus 2. An acoustic sensor array 4 is mounted over the belly, held on in this example by a strap 6. It may instead be temporarily adhered in place.

A processor is provided for processing the detected acoustic sensor signals. In the example shown, the processor is provided in a remote device such as a smart phone 8 to which the sensor signals are transmitted from the sensor array 4 wirelessly. The processor may instead be part of the system, for example a watch-type device. The data communication also may be over a wired connection to the processor rather than wireless. The processing may also be carried out remotely at a central back-end processing location, with communication for example over the internet.

There is a memory for storing the sensor data, and for storing the results of the processing. In the example of FIG. 1, the smart phone 8 implements the memory and processor.

Figure 2:
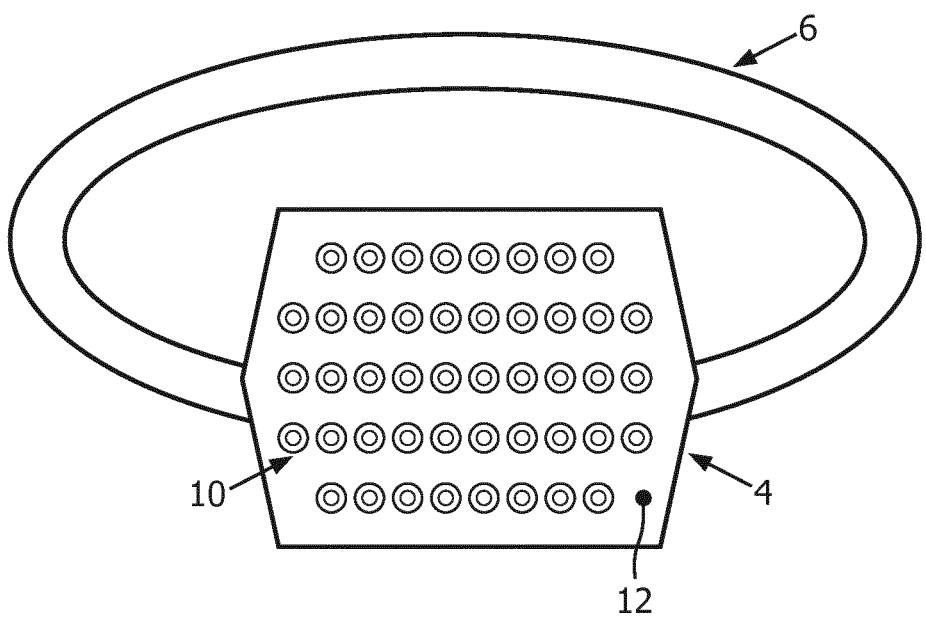
FIG. 2 shows the sensor in more detail.

FIG. 2 shows the sensor 4 in more detail. It comprises an array of microphones 10. The microphones are passive sensors, so that there is no need to provide a signal to the abdomen, as would be required for ultrasound sensing.

The microphones essentially measure air pressure, and other pressure sensors may instead be used, for example contact pressure sensors such as piezoelectric sensors or MEMS sensors.

The microphones 10 may be built in to a textile patch 12 that can be worn on the abdomen of the expectant mother, with the help of any suitable fixation mechanism such as the elastic strap 6. Another option is to embed the sensor array into the abdominal portion of maternity clothes, so that the sensor array becomes an integral part of the clothing. In this case, the sensor array 4 needs to be made washable.

The size of the patch 12 is sufficient to cover the abdomen under which the uterus is located. The inter-sensor distance of the microphone array is typically in the range of a few centimeters, for example 1 to 5 cm, and a two dimensional sensor array is provided. The sensors may be evenly distributed over the patch area but this is not essential. They may for example be more densely packed at the locations where the heart signal is usually strongest.

There is a compromise between the spatial resolution required and the number of microphones (thus the cost and hardware complexity as well as the processing complexity).

The patch 12 is designed to fit the curvature of the abdomen, and therefore the substrate as well as the wiring among sensors must be, to some degree, stretchable and bendable.

There are preferably at least 5 sensors in the array, and preferably more, for example 10 or more, or even 20 or more.

The beating heart of the fetus acts as a sound source, creating a sound wave propagating from the fetal heart outwards. This sound wave arrives at the mother's belly, and is picked up by the sensor array.

Figure 3:
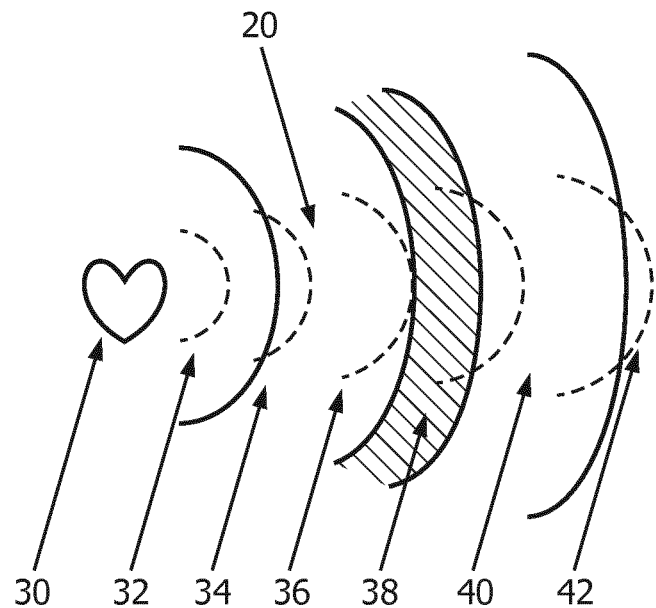
FIG. 3 shows how sound travels from the heart of the fetus to the skin surface of the abdomen of an expectant mother.

As shown in FIG. 3, assuming the heart 30 is a point sound source, the fetal heart generates approximately a spherical wave 20 that passes through the chest of the fetus (including fetus internal tissue 32 and the skin 34), the amniotic fluid 36, the uterine wall 38 and the mother's belly wall 40 and skin 42.

Due to the anisotropic nature of the sound propagating path, the wave front does not remain spherical upon arriving on the belly. The magnitude of the sound field intensity depends on the length of the path followed to reach the belly as well as the composition of the propagation path. A stronger heart sound may be captured by a microphone on the mother's belly that is placed closer to the fetal heart, but this is not necessarily the case. Thus, a single identification of a maximum intensity signal is not a reliable indicator of the position of the heart.

Figure 4:
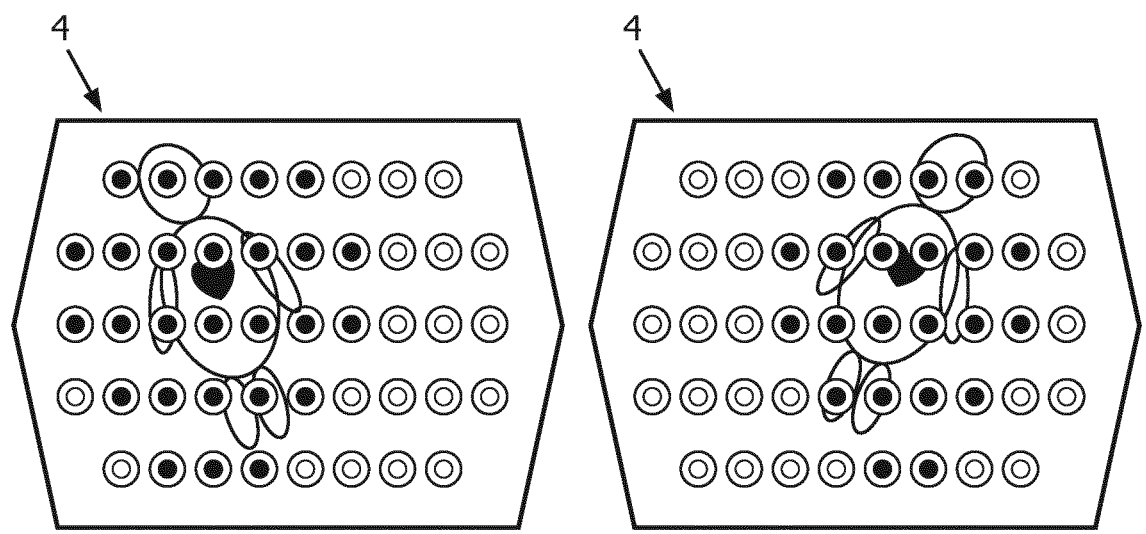
FIG. 4 shows how the position and orientation of the fetus influences the sensor signals.

FIG. 4 shows the sensor array 4 with two fetal positions beneath. An empty (white) central circle represents a low signal, a grey central circle represents a medium signal and a black central circle represents a strong signal. The signal strength drops gradually with distance from the center of distribution, which may correspond to the location of the heart (as is shown in FIG. 4). However, there is no reliable link between the location of any one maximal sound pressure point and the heart location.

A sound signal is captured by each sensor in the array, transmitted to the memory and/or processor and logged as a function over time. The intensity of the sound signal at each sensor may be locally calculated, for instance, by an analogue integrator. The rate of transmission and data logging needs to be sufficiently high in order to capture fetal movement and position changes, which can be in the range of a few to a few tens Hz.

The data processing may be carried out in real time, or it may be performed later based on stored sensor data. The data processing unit reads out the heart sound intensity data from the memory. The data are in the form of a 2-dimensional array, and also a function of time, meaning there is an array of data stored every T seconds, where T is the data logging period.

Thus, every signal in the array is a function of time $s_{i,j}(t)$, where (i,j) denotes the two-dimensional index of the sensor in the array, and all the signals at a same time moment t form a 2-dimensional frame S(t).

The sensor data are actually a collection of temporal and spatial changes of the fetal heart sound.

The data processing includes various signal processing steps, including signal conditioning, and then calculation of the center of distribution, and extraction of the fetal movement and position/orientation information.

The initial signal conditioning is responsible for filtering out noise, which applies to both the individual sensor $s_{i,j}(t)$ signals and the overall frame S(t) signal.

After signal conditioning, the center of distribution C(t): $(i_c(t), j_c(t))$, is calculated from each 2-dimensional frame S(t). The center is defined with reference to the sensor array, i.e. as a row and column index.

This calculation is known to skilled persons in the field and thus not explained in detail.

The center of distribution signal C(t) may be considered directly linked to the position of the fetal heart relative to the sensor array, even though not necessarily at a location on the belly closest to the heart (as a result of different propagation paths). Therefore, from the temporal variation of C(t), information about the fetal movement i.e. position change may be derived. For orientation information, pattern recognition is used since identification of a single point is not sufficient to determine orientation.

The following are some examples of how a fetal movement can be detected, based on tracking the center of distribution.

A threshold is applied to the amount of change in the signal C(t) for two successive sampling times kT and (k+1)T. Thus, when:

$$\|C(t_{(k+1)T})-C(t_{kT})\|>\delta_m \quad \text{(Eq. 1)}$$

a fetal movement is recorded of a duration of T, where $\delta_m$ is a pre-set movement threshold value.

When the above threshold change is sustained for N consecutive pairs of position values a fetal movement of a duration of NT is recorded.

Additional rules may be added to avoid recording of ambiguous movement. For instance, a fetal movement may be identified and recorded only when Eq. 1 above holds consecutively for a certain number of sampling times. In this way, a determined movement is only classified as a movement event when a minimum number of successive predetermined time periods are reached.

A fetal movement event (by which is meant one continuous chain of movements) may also be determined to be finished only when Eq. 1 does not hold consecutively for a certain number of sampling times. In this way, sequential movements are classified as the same movement event if they are separated only by a short interval of no detected movement, i.e. a maximum number of successive periods without detected movement.

The end position can be the same as the starting portion by the end of a movement, according to the criteria defined above.

In order to determine the type of a movement change (which may either be caused by a shift in orientation or a change of the position), movement as represented by C(t) of more than a threshold is identified. Thus, when:

$$\|C(t_{(k+1)T})-C(t_{kT})\|>\delta_p \quad \text{(Eq. 2)}$$

and thereafter the position value stays around $C(t_{(k+1)T})$ for a prolonged time $T_p$, a fetal position change is recorded. $\delta_p$ is a pre-set threshold value that is normally larger than $\delta_m$. The setting of $T_p$ depends on the gestational stage, typically ranging from a few minutes to hours. According to this definition, a position change is a movement of the fetus as a whole towards a certain direction that ends at a different position from that when it begins.

In this way, a determined movement is classified as a fetal position change when the change in center of distribution position exceeds a threshold.

In the third trimester, especially when approaching the final stage of pregnancy, the fetus grows into such a size that it becomes more restricted in the uterus. A position change is not easy at this stage, and is also slow, and most often only relates to a change of the presenting part of the fetus relative to the pelvis of the mother. This movement, with no global position change but with rotation of the fetus, is termed an orientation change.

In this case, the data sampling period $T_o$ takes a significantly larger value, i.e., $T_o \gg T$, up to a few tens of minutes and even hours.

An orientation change is recorded when:

$$\|C(t_{(k+1)T_o})-C(t_{kT_o})\|>\delta_o \quad \text{(Eq. 3)}$$

and the position value stays around $C(t_{(k+1)T_o})$ for a certain number of time periods $T_o$.

Figure 5:
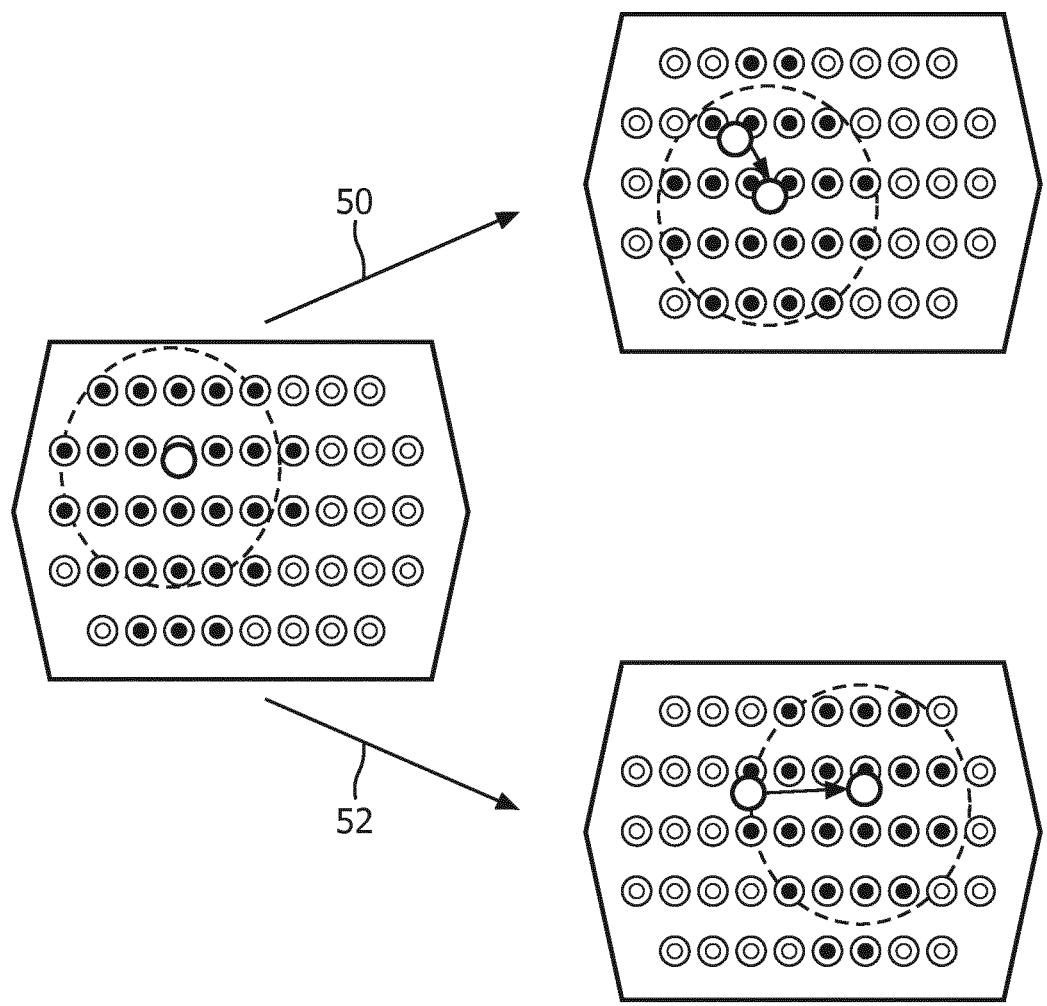
FIG. 5 shows two possible movements.

In FIG. 5, an example of fetal movement 50 and position change 52 is illustrated respectively. All the fetal position changes will be counted as one or multiple fetal movement(s) depending on the timings involved.

The functioning of the system has been simulated. According to the simulation results, the sound intensity distribution projected on the sensor array is asymmetrical.

Besides the method mentioned above, pattern recognition of the sound pressure distribution can also be used to determine both the orientation and the position of the fetus, with a training database of collections of sound pressure patterns. One specific example of distinguishing between head-up and head-down orientations of the fetus by the pattern recognition will now be presented, based on the simulation results.

A complex finite element method (FEM) was established for the simulation. The model includes the physiological parts shown in FIG. 2 but also the placenta, abdominal muscle of the mother, and the heart, spine and ribs of the mother.

The parameters used in this simulation were tissue density values and bulk modulus values, acquired from literature relating to a gestational age of 34 weeks. The values are shown in the table below.

TABLE 1

| Organ | Density (g/cm³) | Bulk Modulus (GPa) |
| --- | --- | --- |
| Pregnancy skin | 1.12 | 2.5 |
| Pregnancy muscle | 1.11 | 2.3 |
| Pregnancy body fluid | 1.01 | 2.2 |
| Pregnancy heart | 1.12 | 2.5 |
| Pregnancy spine and rib | 1.138 | 20 |
| Uterus | 1.12 | 2.18 |
| Placenta | 1.12 | 2.2 |
| Amniotic fluid | 1 | 2.18 |
| Fetus | 1.1 | 10 |
| Fetus heart | 1.12 | 2.5 |

Figure 6:
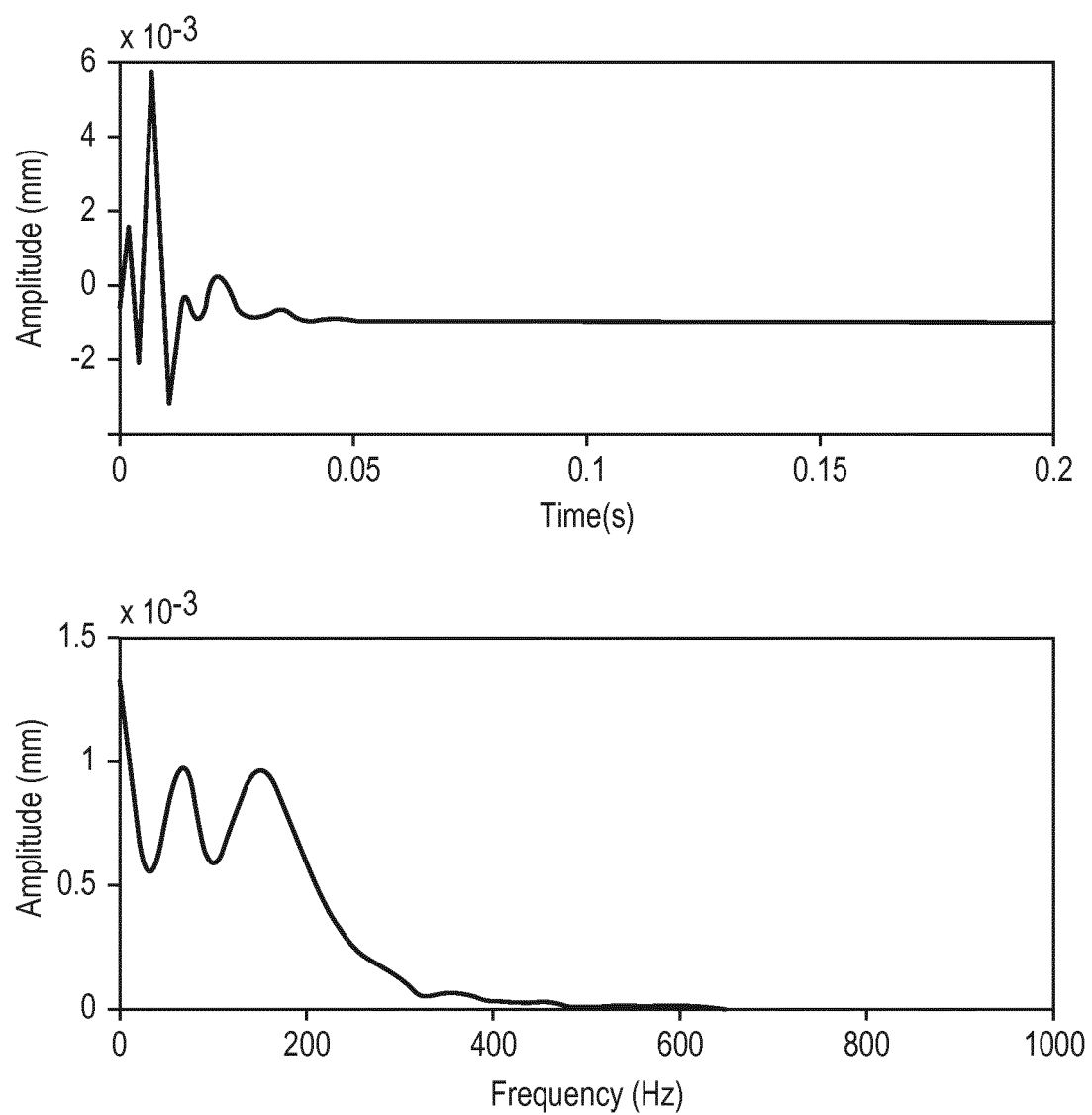
FIG. 6 shows the characteristics of a sound used to simulate a hear beat of a fetus, used for modeling purposes.
Figure 7:
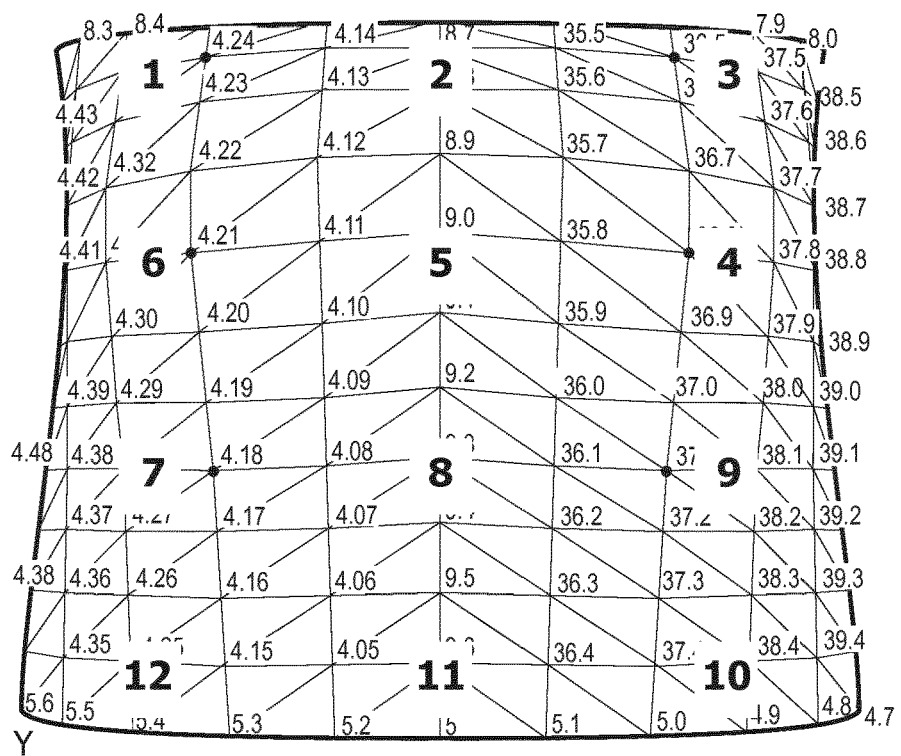
FIG. 7 shows on example of sensor positions over the abdomen.

A heart sound as shown in FIG. 6 was used as input. FIG. 6 shows the amplitude as a function of time (top graph) and as the amplitude a function of frequency (bottom graph). The output on the abdomen is recorded from 12 selected points as schematically shown in FIG. 7. The 12 channels were recorded over time.

Note that for the determination of fetal orientations of head-up or head-down, 12 microphones is enough. However, more may be used for other purposes.

The effective sound pressure of each point was recorded, which is the sound pressure that can be detected by the microphones, integrated over a time period $\Delta t=0.05$ s. This sound pressure is given by:

$$p_{e,i} = \sqrt{\frac{1}{\Delta t}\int_0^{\Delta t} p_i^2 dt} \quad \text{(Eq. 4)}$$

where $p_{e,i}$ is the effective sound pressure recorded by the $i^{th}$ microphone and t is time.

$p_i$ is the instantaneous sound pressure at the abdomen surface at the sensor location. The effective sound pressure is thus defined essentially as a root mean square value.

Figure 8:
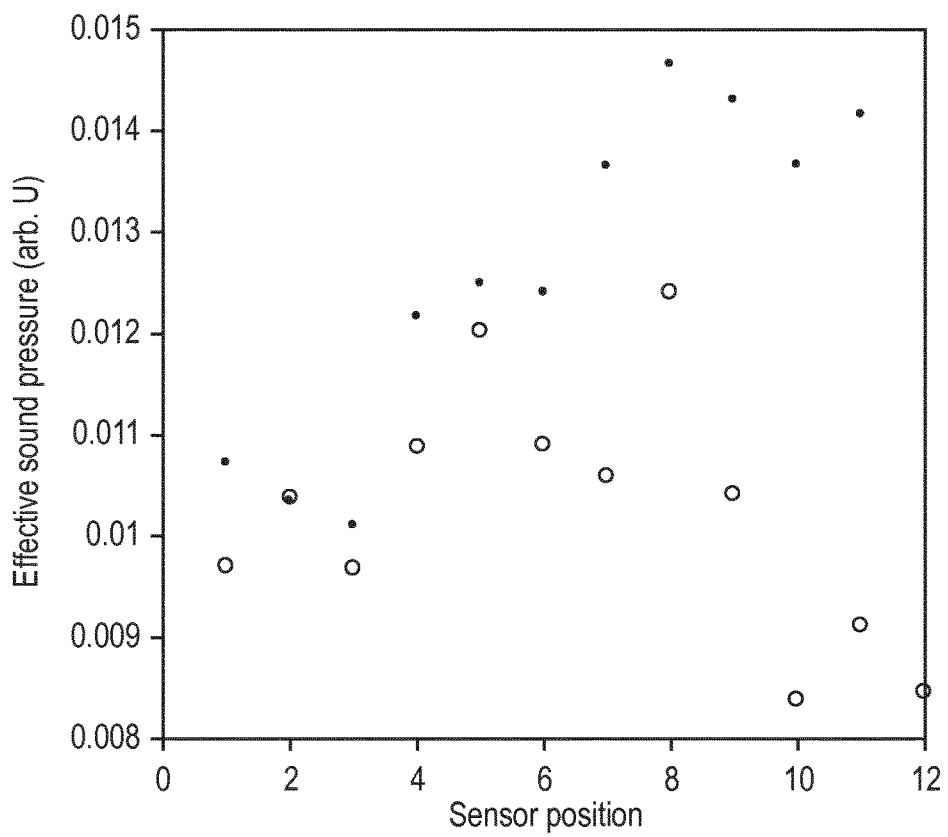
FIG. 8 shows a plot of sound pressure versus sensor position for the arrangement of FIG. 7.

The effective sound pressure from the sensors on the 12 selected points for head-up and head-down orientations are plotted in FIG. 8. The value $p_{e,i}$ is plotted (y-axis) against the sensor number (x-axis).

The head up results are shown as circles and the head down results are shown as dots.

From the results in FIG. 8, it can be seen that the sound pressures of the bottom three sensors (numbers 10-12) are distinctive as between the head-up and head-down cases since the effective acoustic paths have changed dramatically.

To demonstrate how the pattern recognition method functions, 100 sets of data points were been generated for each possible orientation by applying a random noise with Gaussian distribution with a standard deviation of ±5.6%. This is used to estimate the maximal possible density and modulus change that could happen during gestation.

This analysis is based on the acoustic wave motion equation:

$$\rho \frac{\partial v}{\partial t} = -\frac{\partial p}{\partial d} \quad \text{(Eq. 5)}$$

where ρ is the medium density, v is the velocity, t is the time, p is the sound pressure, d is the distance to the sound source.

If the effect of other parameters is ignored, and the density of the medium changes by x %, the sound pressure on the abdominal surface can be roughly estimated by:

$$p_2 = p_1 \pm (|p_0| - |p_1|) \times x\% \quad \text{(Eq. 6)}$$

where $p_1$ is the original sound pressure before the density change and $p_0$ is the sound pressure of the inner heart sound.

The density of the fetus changes during pregnancy, whereas the density of the expectant mother remains essentially constant. These changes can also be taken into account when interpreting the sound pressure signals. Thus, the data processing may evolve over time.

The dataset of 200 data points was used to create a binary classifier (to classify head-up and head-down orientations) and evaluate its performance. Following the same logic a classifier distinguishing more than 2 fetus positions may be generated if there is a need to do so in practice.

In the analysis, the correctly classified instances were 199 out of 200.

Figure 9:
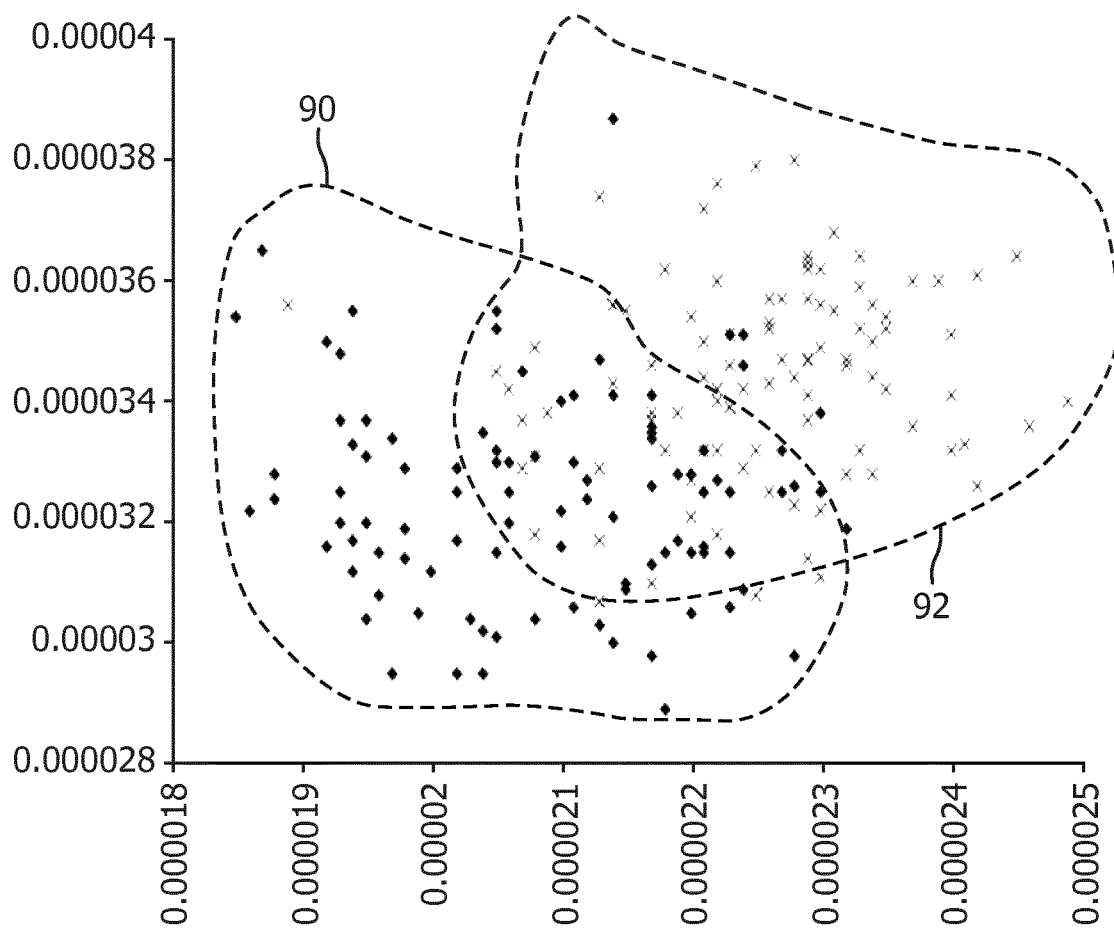
FIG. 9 shows a first plot comparing a first pair of sensor signals of the sensor arrangement of FIG. 7 for two different fetus orientations.

In FIG. 9, a 2-dimensional scatter plots is shown for sensor 5 vs. sensor 3. The y-axis plots the sensor 5 signal and the x-axis plots the sensor 3 signal.

The plots of the head-up orientation are shown with diamonds and are generally in the region 90 whereas the plots for the head-down orientation are shown with crosses and are generally in the region 92. However, there is significant overlap so that sensors 3 and 5 do not easily enable the head-up and head-down orientations to be determined.

Figure 10:
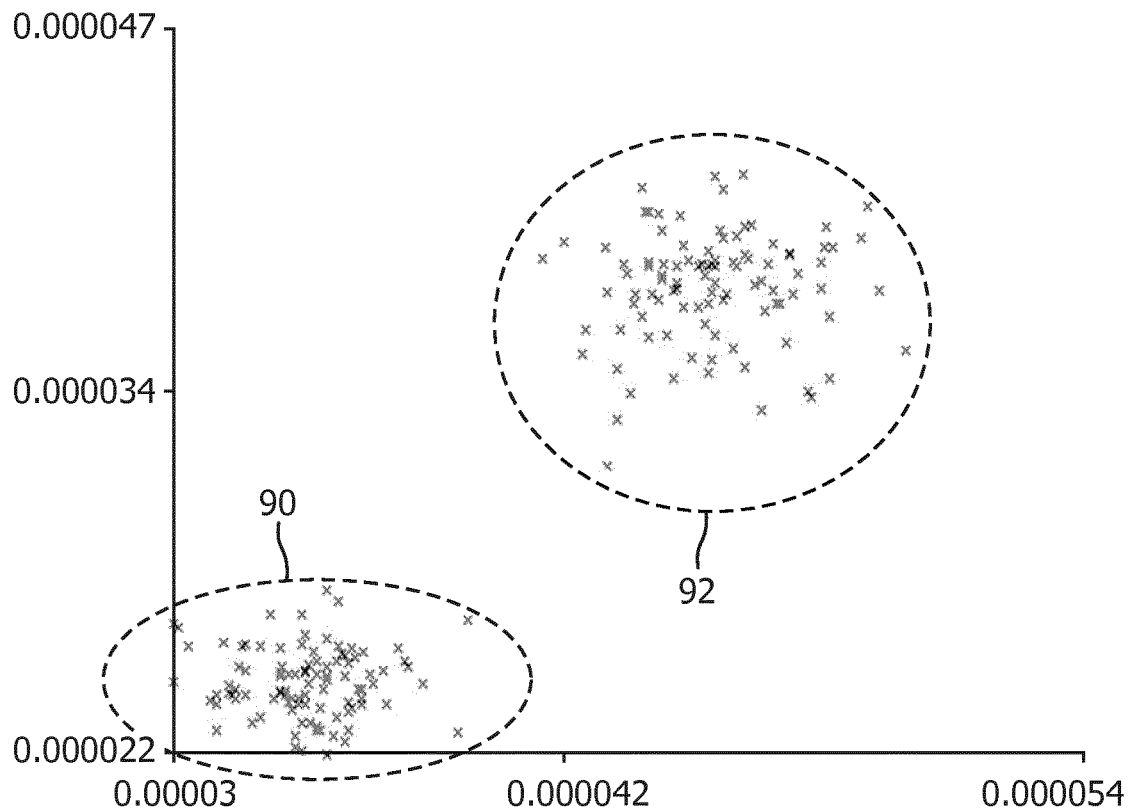
FIG. 10 shows a second plot comparing a second pair of sensor signals of the sensor arrangement of FIG. 7 for two different fetus orientations.

In FIG. 10, a 2-dimensional scatter plots is shown for sensor 7 vs. sensor 8. The y-axis plots the sensor 7 signal and the x-axis plots the sensor 8 signal.

The plots of the head-up orientation are in the region 90 whereas the plots for the head-down orientation are in the region 92. There is no overlap so that sensors 7 and 8 enable the head-up and head-down orientations to be determined.

Figure 11:
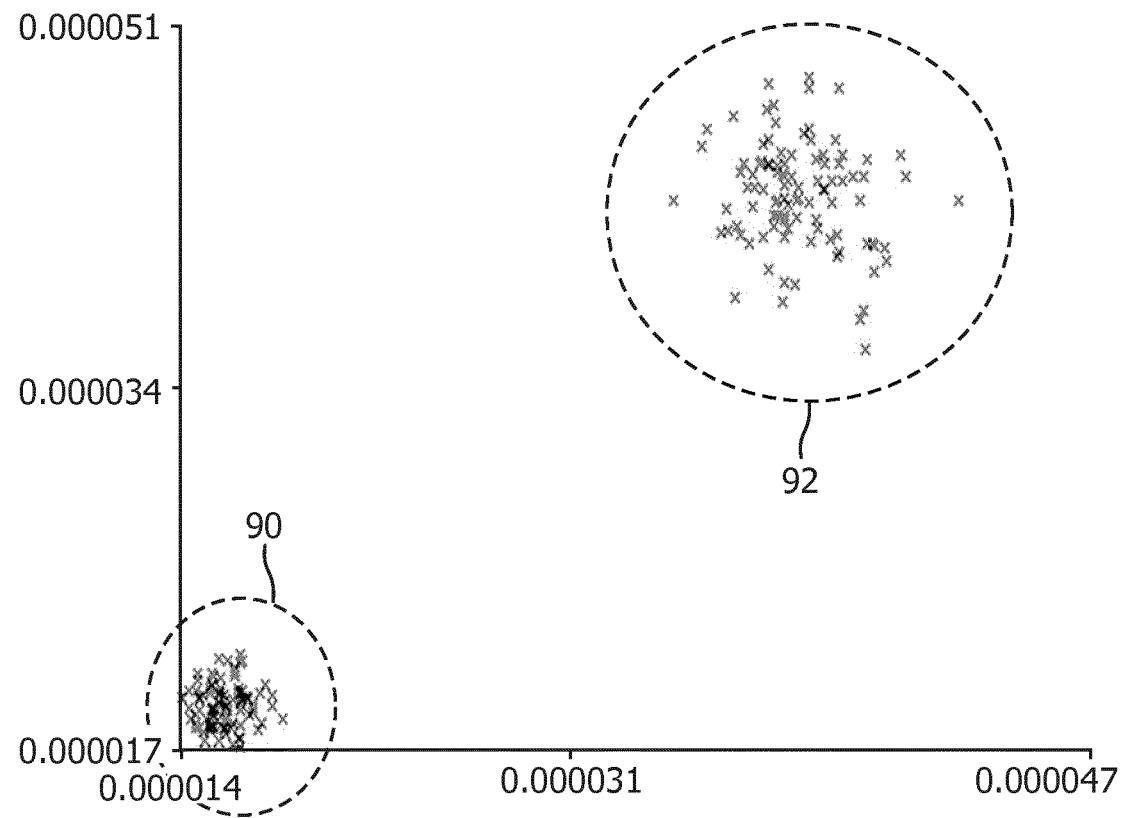
FIG. 11 shows a third plot comparing a third pair of sensor signals of the sensor arrangement of FIG. 7 for two different fetus orientations.
Figure 12:
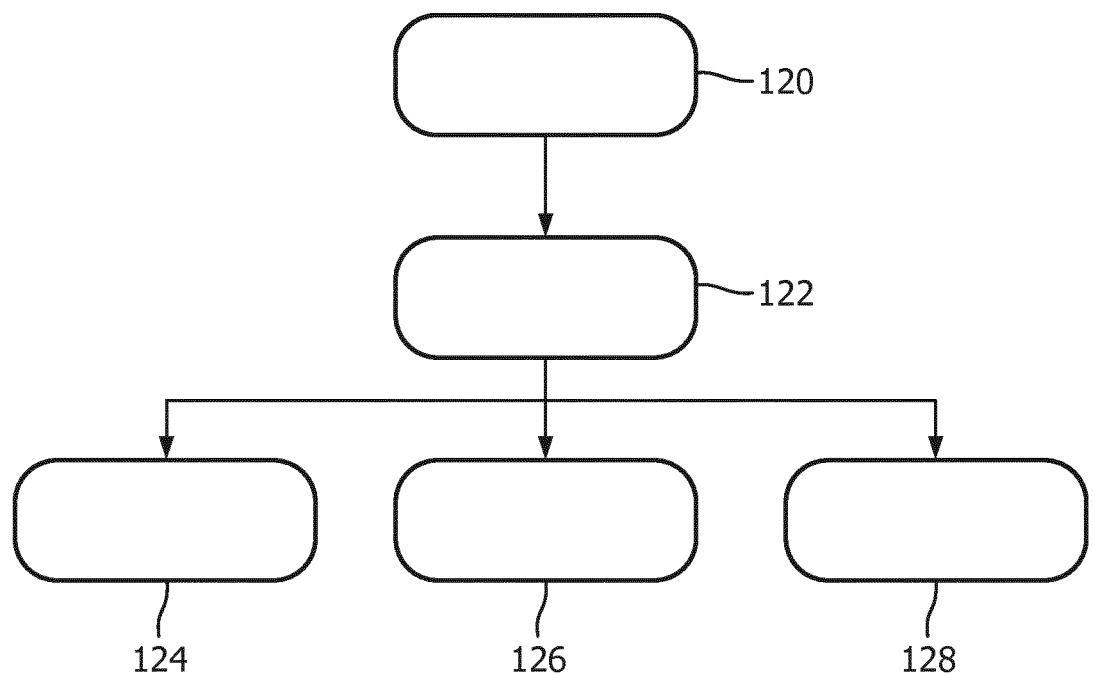
FIG. 12 shows a fetus monitoring method.

In FIG. 11, a 2-dimensional scatter plots is shown for sensor 11 vs. sensor 12. The y-axis plots the sensor 11 signal and the x-axis plots the sensor 12 signal.

The plots of the head-up orientation are in the region 90 whereas the plots for the head-down orientation are in the region 92. There is no overlap so that sensors 11 and 12 enable the head-up and head-down orientations to be determined.

It is thus clear that for distinguishing the head-up from head-down orientation, the signals from the microphones at the bottom of the 3×4 sensor array as illustrated in FIG. 7 can be chosen as features that provide satisfactory performance.

The example above shows that using pattern recognition to identify the fetal orientation can be very promising. Note that only 12 sensors were used for this example but more sensors may be used to lead to higher accuracy of detection. In this example, only readings from each sensor were used as features for classification; other features like the linear combinations of these sensors or the difference between sensors in certain areas can also be fed into the classifier when needed.

In real applications, a predictive model may be established with proper training. The training process could involve detecting and recording the sound pressure pattern of the fetal heart sound on pregnant women's abdomen. Features may then be selected or extracted from these patterns. In this way, a relationship may be formulated between the selected feature(s) and the actual fetal orientations detected by a sonograph.

After having established model from training, actual fetal orientation prediction can be implemented by recording the sound pressure pattern of the fetal heart sounds on the pregnant woman's abdomen. The features are then selected or extracted from the sensed signals, and the fetal orientation is predicted based on the model built up in the training process.

If the system is provided with the sonograph information obtained during regular antenatal check-ups at hospital, this information may be used for calibration purposes. The classifier model may in this way be tailor-made to suit more a specific person, which leads to an improved accuracy.

Determining the fetal orientation may also be used to derive a fetal position, instead of relying on the center of distribution as described above. A training database with collections of sound pressure patterns associated with different fetal positions can be established as the training process. A classifier algorithm giving the fetal position can be determined in a similar way as the fetal orientation described above.

Thus, orientation can be determined by a classifier applied to the sound pressure distribution, with or without also determining the center of distribution. The position (or position change) can be determined either based on the center of distribution alone or based on a classifier in the same way as the orientation.

As explained above, the data detected by the sensors may be transmitted to a memory in a wired or wireless fashion. The data transmitted can be analogue or converted to digital prior to the transmission. Transmission is carried out at the pre-defined data logging rate, typically a few Hz that is sufficient for capturing the wanted fetal activity information. If power savings are desired and/or minimizing radiation, wired transmission will be used preferred.

The data storage unit stores the data collected by the detection unit as well as the analysis results from the data processing unit. It can be a wearable storage medium wirelessly or in a wired fashion connected to the detection unit.

The display device unit uses the analysis results stored in the memory, and communicates with the user (mother-to-be and/or family members) by visualizing the fetal activity info on the display. The content of the visualization may include the amount of fetal movement, the trajectory of the fetal position/orientation change, and overall fetal activity level, as a function of time. Warnings can be provided if, for instance, the amount of fetal movement is below the limit, or the position of the fetal seems not optimal when approaching the expected delivery date. The communication to the user can be provided upon a request from the user, or instantly if an immediate warning is necessary.

The system described above makes use of a controller or processor for processing the sensed data and for performing the data analysis.

Figure 13:
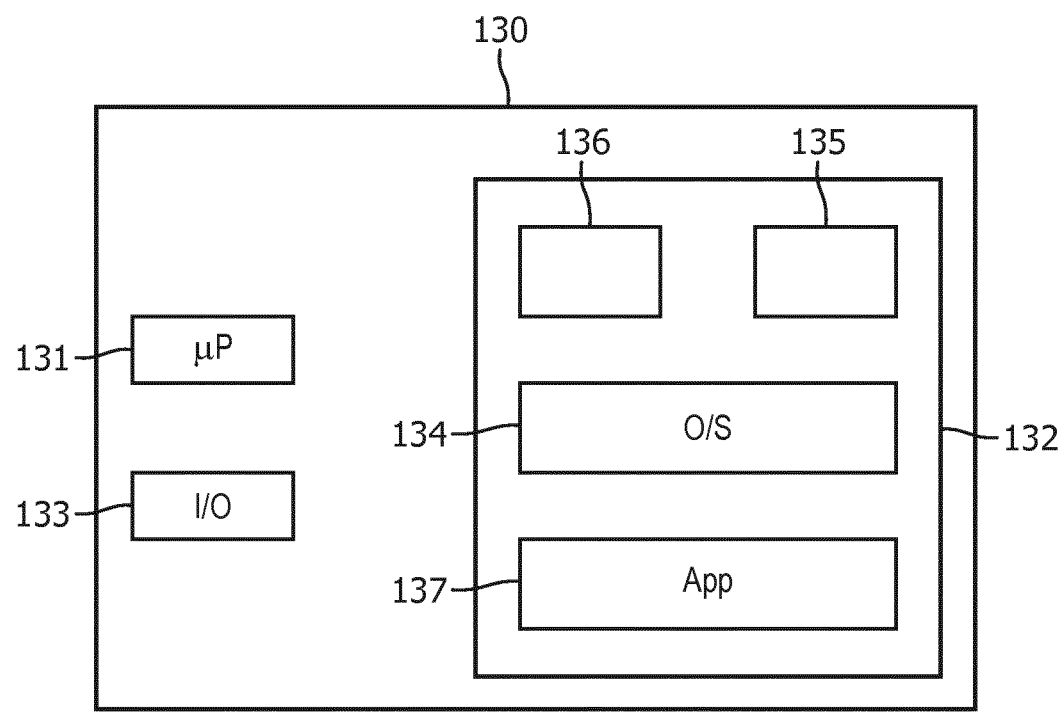
FIG. 13 shows a general computer architecture which may be used to implement the processing in the system.

FIG. 13 illustrates an example of a computer 130 for implementing the controller or processor described above.

The computer 130 includes, but is not limited to, PCs, workstations, laptops, PDAs, palm devices, servers, storages, and the like. Generally, in terms of hardware architecture, the computer 130 may include one or more processors 131, memory 132, and one or more I/O devices 133 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 131 is a hardware device for executing software that can be stored in the memory 132. The processor 131 can be virtually any custom made or commercially available processor, a central processing unit (CPU), a digital signal processor (DSP), or an auxiliary processor among several processors associated with the computer 130, and the processor 131 may be a semiconductor based microprocessor (in the form of a microchip) or a microprocessor.

The memory 132 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 132 may incorporate electronic, magnetic, optical, and/or other types of storage media. Note that the memory 132 can have a distributed architecture, where various components are situated remote from one another, but can be accessed by the processor 131.

The software in the memory 132 may include one or more separate programs, each of which comprises an ordered listing of executable instructions for implementing logical functions. The software in the memory 132 includes a suitable operating system (O/S) 134, compiler 135, source code 136, and one or more applications 137 in accordance with exemplary embodiments.

The application 137 comprises numerous functional components such as computational units, logic, functional units, processes, operations, virtual entities, and/or modules.

The operating system 134 controls the execution of computer programs, and provides scheduling, input-output control, file and data management, memory management, and communication control and related services.

Application 137 may be a source program, executable program (object code), script, or any other entity comprising a set of instructions to be performed. When a source program, then the program is usually translated via a compiler (such as the compiler 135), assembler, interpreter, or the like, which may or may not be included within the memory 132, so as to operate properly in connection with the operating system 134. Furthermore, the application 137 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 133 may include input devices such as, for example but not limited to, a mouse, keyboard, scanner, microphone, camera, etc. Furthermore, the I/O devices 133 may also include output devices, for example but not limited to a printer, display, etc. Finally, the I/O devices 133 may further include devices that communicate with both inputs and outputs, for instance but not limited to, a network interface controller (NIC) or modulator/demodulator (for accessing remote devices, other files, devices, systems, or a network), a radio frequency (RF) or other transceiver, a telephonic interface, a bridge, a router, etc. The I/O devices 133 also include components for communicating over various networks, such as the Internet or intranet.

When the computer 130 is in operation, the processor 131 is configured to execute software stored within the memory 132, to communicate data to and from the memory 132, and to generally control operations of the computer 130 pursuant to the software. The application 137 and the operating system 134 are read, in whole or in part, by the processor 131, perhaps buffered within the processor 131, and then executed.

When the application 137 is implemented in software it should be noted that the application 137 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The system and method described above may be used for fetal/pregnancy monitoring products.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A system for monitoring fetal movement of a fetus of a pregnant woman, comprising:
   an acoustic sensor array positioned over a belly of the pregnant woman, wherein the acoustic sensor array comprises at least one acoustic sensor, each acoustic sensor of the acoustic sensor array configured to continuously receive at least one acoustic sensor signal generated by the fetal heartbeat over multiple predetermined time periods; and
   a processor;
   a tangible, non-transitory computer readable medium that stores instructions, which when executed by the processor, causes the processor to:
   determine and identify a geometric center of spatial distribution from the received acoustic sensor signal for each predetermined time period;

determine fetal movement by detecting a change in a position of the geometric center of the spatial distribution over the multiple predetermined time periods; and classify the determined fetal movement as a fetal position change when the change in the position of the geometric center of the spatial distribution exceeds a threshold.

2. The system as claimed in claim 1, wherein the acoustic sensor array comprises an array of passive sound sensors.

3. The system as claimed in claim 1, wherein the instructions when executed by the processor, further cause the processor to determine a duration of a movement event by counting a number of successive predetermined time periods during which there is determined fetal movement.

4. The system as claimed in claim 3, wherein the instructions when executed by the processor, further cause the processor to:
classify a determined movement as a movement event when a minimum number of successive predetermined time periods is reached; and/or
classify sequential movements as the same movement event if the sequential movements are separated by a number of successive predetermined time periods without detected movement, wherein the number of successive predetermined time periods does not exceed a preset value.

5. The system as claimed in claim 1, wherein the instructions when executed by the processor, further cause the processor to classify a determined movement as a change in at least one of a fetal orientation or a fetal position by pattern recognition based on a training database of acoustic signal distributions, wherein: the fetal orientation refers to an angle between a fetal long axis to a long axis of the pregnant woman; and the fetal position refers to a location of the fetus relative to the geometric center of the pregnant woman's abdomen.

6. The system as claimed in claim 1, further comprising:
a data transmitter for transmitting the acoustic sensor signal data to the processor or to the tangible, non-transitory computer readable medium, by a wired or a wireless link.

7. A system as claimed in claim 1, further comprising a user interface for presenting results of the processing to a user.

8. A method for monitoring the fetal movement of a fetus of a pregnant woman, comprising:
receiving, via an array of acoustic sensors located proximate to a belly of the pregnant woman, acoustic sensor signals continuously over multiple predetermined time periods;
determining and identifying, via a processor connected to the array of acoustic sensors, a geometric center of spatial distribution from the received acoustic sensor signals for each predetermined time period;
determining, via the processor, a fetal movement by detecting a change of a position of the geometric center of the spatial distribution over the multiple predetermined time periods; and
classifying the determined fetal movement as a fetal position change when the change of the position of the geometric center of the spatial distribution exceeds a threshold.

9. The method as claimed in claim 8, further comprising determining a duration of a movement event by counting a number of successive predetermined time periods during which there is determined fetal movement.

10. The method as claimed in claim 9, further comprising:
classifying a determined movement as a movement event when a minimum number of successive predetermined time periods is reached and/or to classify sequential movements as the same movement event if the sequential movements are separated by a number of successive predetermined time periods without detected movement, wherein the number of successive predetermined time periods does not exceed a preset value.

11. The method as claimed in claim 8, further comprising:
classifying a determined movement as fetal orientation change or fetal position change by pattern recognition based on a training database of acoustic signal distributions, wherein: the fetal orientation refers to an angle between a fetal long axis to a long axis of the pregnant woman; and the fetal position refers to a location of the fetus relative to the geometric center of the pregnant woman's abdomen.

12. The method of claim 8, wherein the processor and the array of acoustic sensors are wirelessly connected.

13. A tangible, non-transitory computer readable medium that stores instructions, which when executed by a processor, causes the processor to execute a method of monitoring a fetal movement of a fetus of a pregnant woman, comprising:
receiving, via an array of acoustic sensors located proximate to a belly of the pregnant woman, acoustic sensor signals continuously over multiple predetermined time periods;
determining and identifying a geometric center of spatial distributions from the received acoustic sensor signals for multiple predetermined time periods;
determine the fetal movement by detecting a change in a position of the geometric center of the spatial distribution over the multiple predetermined time periods; and
classifying the determined fetal movement as a fetal positon change when the change in the position of the geometric center of the spatial distribution exceeds a threshold.

14. The tangible, non-transitory computer readable medium of claim 13, wherein the instructions when executed by the processor, further cause the processor to execute the method, which further comprises determining a duration of a movement event by counting a number of successive predetermined time periods during which there is determined fetal movement.

15. The tangible, non-transitory computer readable medium of claim 14, wherein the instructions when executed by the processor, further cause the processor to execute the method, which further comprises:
classifying a determined movement as a movement event when a minimum number of successive predetermined time periods is reached; and/or
classifying sequential movements as the same movement event if the sequential movements are separated by a number of successive predetermined time periods without detected movement, wherein the number of successive predetermined time periods does not exceed a preset value.

* * * * *